(12) United States Patent
Florent et al.

(10) Patent No.: US 8,554,308 B2
(45) Date of Patent: Oct. 8, 2013

(54) PHASE-FREE CARDIAC ROADMAPPING

(75) Inventors: Raoul Florent, Ville Davray (FR);
Stephane Valente, Paris (FR)

(73) Assignee: Koninklijke Philips N.V., Eindhoven (NL)

( * ) Notice: Subject to any disclaimer, the term of this patent is extended or adjusted under 35 U.S.C. 154(b) by 508 days.

(21) Appl. No.: 12/528,097

(22) PCT Filed: Feb. 25, 2008

(86) PCT No.: PCT/IB2008/050668
§ 371 (c)(1),
(2), (4) Date: Jan. 25, 2010

(87) PCT Pub. No.: WO2008/104921
PCT Pub. Date: Sep. 4, 2008

(65) Prior Publication Data
US 2010/0145193 A1    Jun. 10, 2010

(30) Foreign Application Priority Data
Feb. 28, 2007  (EP) ..................................... 07103243

(51) Int. Cl.
*A61B 5/00* (2006.01)
(52) U.S. Cl.
USPC .......................... 600/427; 345/629; 345/643
(58) Field of Classification Search
USPC ................. 600/407, 425, 427; 382/128, 131; 345/418, 619, 629, 643
See application file for complete search history.

(56) References Cited

U.S. PATENT DOCUMENTS

| | | | |
|---|---|---|---|
| 5,274,551 | A | 12/1993 | Corby |
| 6,351,513 | B1 | 2/2002 | Bani-Hashemi et al. |
| 2005/0004454 | A1 | 1/2005 | Mitschke et al. |
| 2005/0197568 | A1 | 9/2005 | Vass et al. |
| 2006/0036167 | A1 | 2/2006 | Shina |
| 2006/0058643 | A1 | 3/2006 | Florent et al. |
| 2006/0257006 | A1 | 11/2006 | Bredno et al. |
| 2007/0003014 | A1 | 1/2007 | Boese et al. |

FOREIGN PATENT DOCUMENTS

| | | |
|---|---|---|
| WO | 2004034329 A2 | 4/2004 |
| WO | 2005039253 A1 | 4/2005 |
| WO | 2006103644 A1 | 10/2006 |

OTHER PUBLICATIONS

Buecker et al: "Simultaneous Real-Time Visualization of the Catheter Tip and Vascular Anatomy for MR-Guided PTA of Iliac Arteries in an Animal Model"; Journal of Magnetic Resonance Imaging, vol. 16, pp. 201-208, 2002.
Frangi et al: "Multiscale Vessel Enhancement Filtering"; Lecture Notes in Computer Science, vol. 1496, pp. 130-137, 1998.
Bredno et al: "Algorithmic Solutions for Live Device-to-Vessel Match"; Medical Imaging 2004: Image Processing, J.M. Fitzpatrick, Milan Sonka (Eds), Proceedings of SPIE, vol. 5370, pp. 1486-1497, May 2004.

*Primary Examiner* — Ruth S Smith

(57) ABSTRACT

According to an exemplary embodiment of the present invention, a cardiac roadmapping technique is provided, that does not rely on the prerequisite of a phase-centric pairing of the angiogram and life images. Instead, both the pairing and accurate registration of the images are combined within a single operation, for example by using a multi-device map. This may provide for robust and precise cardiac roadmapping.

9 Claims, 3 Drawing Sheets

PHASE-FREE CARDIAC ROADMAPPING

The invention relates to the field of interventional imaging. In particular, the invention relates to an examination apparatus for cardiac roadmapping for examination of an object of interest, to a method for cardiac roadmapping, a computer-readable medium, a program element and an image processing device.

For treating cardiac stenoses, an imaging system for PTCA (Percutaneous Transluminal Coronary Angioplasty) may be used in catheter laboratories. In the following, a basic interventional procedure is described, which can be found in [3]:

"After a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries. Diagnosis and intervention planning are based on such diagnostic angiograms ( . . . ). During intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire ( . . . ) and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled."

In [3], an overlay technique between the angiogram and the live images (referred to as roadmapping) is described:

"In such procedures, the vessel structure itself is not visible during the intervention as it is not radio-opaque. Consequently, the navigation and precise positioning of guidewire and interventional devices is tedious, time-consuming, and requires additional contrast agent bursts to clarify the position of the devices relative to the relevant vessels. Due to scatter, both patient and medical staff are exposed to x-ray during the acquisition of diagnostic angiograms and interventional fluoroscopy. Consequently, navigation support is desired to reduce the intervention time and to enhance the positioning accuracy. Routinely, a static diagnostic angiogram acquired with a similar imager geometry is displayed next to the live interventional fluoroscopy. For the navigation of guidewire and devices within the vessels, a subjective visual fusion of the static angiogram and the live fluoroscopy is required. An improved context-rich visualization could give important support in navigation. As a straightforward approach, preprocessed angiograms can be overlaid onto the fluoroscopic image stream so that vessels and the interventional devices are synchronously displayed on one screen. However, between the acquisition of diagnostic angiograms and the fluoroscopy, time has passed and unintended as well as deliberate patient movements result in changes of position and orientation as well as soft tissue deformation. For coronary interventions, also the vessel structure continuously changes due to heart beat and respiration movement. Consequently, such overlay techniques suffer from mismatches of interventional fluoroscopy and diagnostic overlay ( . . . ). As a result, guidewire and interventional devices are not displayed inside a vessel, the perceived quality of the overlay images is poor."

A navigation system may therefore help the cardiologists by providing a cardiac roadmap displayed next or overlaid on the live fluoroscopy pictures. Ideally, this cardiac roadmap represents the vessel network acquired during angiography, with the same cardiac phase than the current live image.

Documents [1] and [2] describe a basic method for realising cardiac roadmapping. They rely on the extraction of the cardiac and respiratory cycles, and on the matching of those cycles between the angiogram images (in filled state) and the live images.

However, the cycle-centric method described in [1], [2] may not be perfect. Errors may strongly show when an intra-coronary intervention device does not lie within the roadmap. This is typically the case for the guidewire tip. This radio-opaque short metallic part is the intervention device's head. To correctly steer one's way through the vascular network under roadmapping support, the cardiologist may indeed rely on the guidewire tip being accurately located in accordance with the roadmapping data.

In [3] a refinement of [1], [2] is proposed that consists in registering the guidewire tip with the roadmapping data. For this, a vessel map is computed from the angiogram image that corresponds to the considered live image (this correspondence being established for instance following the cycle-centric approach of [1], [2]), and the guidewire tip is extracted from the live image. The extracted tip is then brought into registration with the vessel map. This may help to improve the correct matching between the roadmap and the intervention device.

It would be desirable to have an improved registration of an angiogram sequence and a life-time sequence.

The invention provides an examination apparatus for cardiac roadmapping for examination of an object of interest, an image processing device, a computer-readable medium, a program element and a method of examining an object of interest with the features according to the independent claims.

It should be noted that the following described exemplary embodiments of the invention apply also for the method of examination of the object of interest, for the computer-readable medium, for the image processing device and for the program element.

According to a first aspect of the present invention, an examination for cardiac roadmapping for examination of an object of interest is provided, the examination apparatus comprising a determination unit adapted for performing a cardiac roadmapping on the basis of at least one of a global correlation determination of a first image sequence of the object of interest and a second image sequence of the object of interest, and a correlation determination of a first image of the object of interest and a second image of the object of interest on the basis of an identification of a first object and a second object in the first image and the second image.

In other words, a registration of whole image sequences may be performed globally without having to perform an image selection or pairing in a first step followed by an image registration in a second step.

Therefore, a cardiac roadmapping technique is provided that does not rely on the prerequisite of a phase-centric pairing of the angiogram and life images. Instead, both the pairing and accurate registration of the angiogram and life images are combined within a single operation.

This operation may comprise a global registering of a device-map sequence, incrementally built at life-time, with a vessel-map sequence built during angiogram creation. This global motion-compensated association process may rely on map similarities, but may also enforce temporal coherency.

Alternatively or additionally, the cardiac roadmapping is based on object enhancement, in which case two or more objects are identified in the life-image and in the angiogram image in order to provide for an image registration, i.e. correlation determination. No phase measuring is necessary.

According to another exemplary embodiment of the present invention, the first image is a vessel-map derived from an angiogram of the object of interest and the second image is a life device-map.

Therefore, a registration of the vessel-map and the device-map may be provided without involving an extra pairing or phase measuring step.

According to another exemplary embodiment of the present invention, the second image is binary or multi-valued, reflecting a likelihood of the presence of the first object and the second object.

Furthermore, according to another exemplary embodiment of the present invention, the object of interest is a vessel-tree, wherein the first object is a catheter injection tip at a pivotal point of a vessel-tree and the second object is a guidewire or a balloon marker or a stand marker inserted into a coronary of the vessel-tree.

Furthermore, according to another exemplary embodiment of the present invention, the examination apparatus is adapted for issuing an alarm if no detection of the first object or the second object is performed.

In other words, in case one of the two objects, i.e. the injection tip or the guidewire are unintentionally removed from the examination volume, i.e. the vessel-tree, an alarm signal is generated to warn the user.

According to another exemplary embodiment of the present invention, the first image sequence is a vessel-map sequence and the second image sequence is a device-map sequence.

According to another exemplary embodiment of the present invention, the device-map sequence is a life-time sequence acquired during an intervention of the object of interest.

According to another exemplary embodiment of the present invention, the global correlation determination comprises a definition of a class of geometrical transforms.

Such a class of geometrical transforms may, for example, be the class of all the translations belonging to a certain range. Furthermore, the class may comprise other rigid transforms, such as rotation or shearing, or even non-rigid transforms.

According to another exemplary embodiment of the present invention, the global correlation determination comprises a comparison of device-maps of the device-map sequence to vessel-maps of the vessel-map sequence, resulting in a similarity $S[D_i, V_j, T_k]$ between each device-map of the device-map sequence and each vessel-map of the vessel-map sequence.

For example, within the bound of the transformation class, all the geometrically transformed causal device-maps may be compared via a given similarity criterion to all the vessel-maps of the useful angiogram part.

According to another exemplary embodiment of the present invention, the global correlation determination comprises an optimization of a measure function $K[A]$, which relates to the similarity.

Furthermore, according to another exemplary embodiment of the present invention, the optimization of the measure function enforces a temporal coherency $H[A]$.

Furthermore, the device-map sequence may be a causal device-map sequence.

According to another exemplary embodiment of the present invention, the vessel-map sequence is generated from one of an angiogram data set and an isolated sub-set of the angiogram data set, wherein the vessel-map sequence comprises a plurality of vessel-map images.

Furthermore, according to another exemplary embodiment of the present invention, the vessel-map image of the vessel-map sequence is generated on the basis of a vessel-enhanced image.

Furthermore, according to another exemplary embodiment of the present invention, each vessel-map image of the vessel-map sequence is computed on the basis of a full isolated sub-set of the angiogram data set.

According to another exemplary embodiment of the present invention, an isolation of a sub-set of the angiogram data set is performed on the basis of at least one of a histogram-based procedure and a threshold-based procedure.

According to another exemplary embodiment of the present invention, the device-map sequence is generated from a life-image data set.

Furthermore, the device-map sequence may be generated on the basis of at least one of a position of a guidewire or a marker.

According to another exemplary embodiment of the present invention, the examination apparatus is configured as one of the group consisting of a material testing apparatus, a medical application apparatus and a micro CT system. A field of application of the invention may be medical imaging or baggage inspection.

According to another exemplary embodiment of the present invention, the examination apparatus is adapted as one of a three-dimensional computed tomography apparatus and a three-dimensional rotational x-ray apparatus.

Furthermore, according to another exemplary embodiment of the present invention, a method for cardiac roadmapping for examination of an object of interest with an examination apparatus is provided, in which a cardiac roadmapping is performed on the basis of at least one of a global correlation determination of a first image sequence of the object of interest and a second image sequence of the object of interest and a correlation determination of a first image of the object of interest and the second image of the object of interest on the basis of an identification of a first object and a second object in the first image and the second image.

This may provide for a registration method that is not phase-centric.

According to another exemplary embodiment of the present invention, an image processing device for cardiac roadmapping for examination of an object of interest is provided, the image processing device comprising a memory for storing a data set of the object of interest and which is adapted for carrying out the above-mentioned method steps.

According to another exemplary embodiment of the present invention, a computer-readable medium is provided, in which a computer program for cardiac roadmapping is stored which, when being executed by a processor, causes the processor to carry out the above-mentioned method steps.

Furthermore, according to another exemplary embodiment of the present invention, a program element for cardiac roadmapping for examination of an object of interest is provided, when being executed by a processor, causes the processor to carry out the above-mentioned method steps.

Those skilled in the art will readily appreciate that the method of examination of the object of interest may be embodied as the computer program, i.e. by software, or may be embodied using one or more special electronic optimization circuits, i.e. in hardware, or the method may be embodied in hybrid form, i.e. by means of software components and hardware components.

The program element according to an exemplary embodiment of the invention may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that a registration of images relating to an angiogram data set and images relating to a life-time data set is performed without an additional pairing or image selection step. No identification of a cardiac or respiration phase has to be performed. Therefore, an electrocardiogram or lung monitoring equipment is not necessary.

These and other aspects of the present invention will become apparent from and elucidated with reference to the embodiments described hereinafter.

Exemplary embodiments of the present invention will now be described in the following, with reference to following drawings.

The illustration in the drawings is schematic. In different drawings, similar or identical elements are provided with the same reference numerals.

Figure 1:
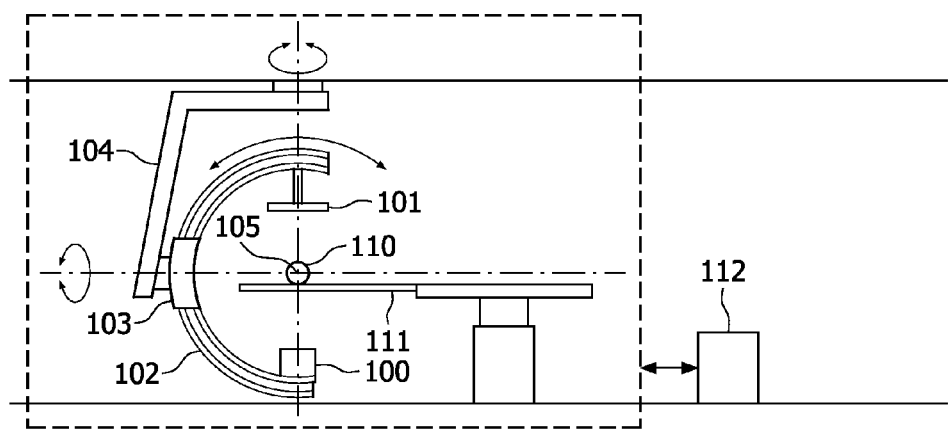
FIG. 1 shows a simplified schematic representation of a C-arm rotational x-ray examination apparatus according to an exemplary embodiment of the present invention.

FIG. 1 shows a schematic representation of an exemplary rotational X-ray scanner in which a method according to the invention may be implemented. An X-ray source 100 and a flat detector 101 with a large sensitive area are mounted to the ends of a C-arm 102. The C-arm 102 is held by curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are effected by servo motors. The axes of the three rotational movements and the cone-beam axis always meet in a single fixed point, the "isocenter" 105 of the rotational X-ray scanner. There is a certain volume around the isocenter that is projected by all cone beams along the source trajectory. The shape and size of this "volume of projection" (VOP) depend on the shape and size of the detector and on the source trajectory. In FIG. 1, the ball 110 indicates the biggest isocentric ball that fits into the VOP. The object (e.g. a patient or an item of baggage) to be imaged is placed on the table 111 such that the object's VOI fills the VOP. If the object is small enough, it will fit completely into the VOP; otherwise, not. The VOP therefore limits the size of the VOI.

The various rotational movements are controlled by a control unit 112. Each triple of C-arm angle, sleeve angle, and L-arm angle defines a position of the X-ray source. By varying these angles with time, the source can be made to move along a prescribed source trajectory. The detector at the other end of the C-arm makes a corresponding movement.

Figure 2:
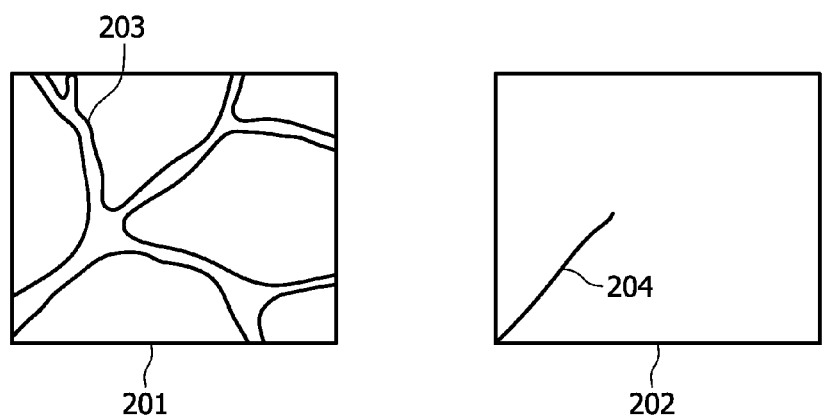
FIG. 2 shows a schematic representation of an angiography-sequence and a life-sequence for registration according to an exemplary embodiment of the present invention.

FIG. 2 shows a schematic representation of an image 201 of an angiography-sequence and an image 202 of a life-sequence for registration according to an exemplary embodiment of the present invention. The image 201 shows the vessel-tree 203 and the image 202, which is acquired during an intervention, shows a guidewire 204 inserted into the vessel-tree 203.

The solution for overlaying angiogram and life images, as proposed in [3], may be limited because it targets a single intervention device, namely the guidewire tip. The uniqueness of the extracted device is made explicit throughout the paper by the recurrent usage of the singular:

In 2.: The extraction of vessels and device or guidewire . . .

In 3.2: During real-time processing, the relevant object . . .

In 6.: This approach (extract vessels and device, then match these objects) . . .

Now, in PTCA interventions, only the tip of the guidewire is sufficiently radio-opaque to be plausibly extracted (as opposed to the full wire). It follows that the targeted device has a very limited breadth as compared to the breadth of vessels in the filled angiogram. As a matter of fact, this also applies to other possible intervention devices such as the balloon markers (mentioned once in [3]), or the catheter injection tip from where the contrast agent flows into the coronaries (the catheter is not mentioned in [3] as a possible targeted device).

Unfortunately, the discrepancy between the breadth of the vessels in the angiogram image and the breadth of the segmented object in the corresponding live image may be bound to lead to high registration inaccuracies. For instance, if the tip is rather straight (which is very often the case), it can reasonably fit into any straight vessel section that shows the same orientation (assuming a simple translation-based registration process). This of course may end up to a highly undiscriminating situation, prone to considerable registration mistakes.

The present invention may improve this situation and may suppress the high degree of inaccuracy of the method described in [3].

According to an aspect of the present invention, several intervention objects are simultaneously present and detected (or enhanced). This may improve the registration of the roadmap and of the live image during cardiac roadmapping.

In particular, the invention proposes to enforce the presence of catheter injection tip in both the angiogram and the live image and to combine the injection tip detection with the detection of another intervention device such as the guidewire tip and/or balloon/stent markers.

The privileged location of the injection tip at a pivotal point of the vessel network anatomy, combined with a more distal device location such as the guidewire tip's location is an essential element for the robustness of the angiogram vessel map and of a multi-device map.

In the routinely used PTCA protocol, the injection tip is not necessarily present in both the angiogram and the live image. According to an exemplary embodiment of the invention the intervention protocol is slightly modified to enforce this presence in both the angiogram and the live image, together with the presence of a second intervention device in the live image. This may improve the vessel-to-device registration operation.

Besides protocol changing, the detection and registration methods proposed by this invention differ from [3] in that the well-identified nature of the involved objects may allow for higher specificity at the detection phase, and lower complexity at the registration phase (see below).

The invention both proposes an interventional protocol constraint and a detection/registration method for cardiac roadmapping.

Protocol Constraint:

An aspect of the invention stipulates that two distinct devices should be present in the live image, and their corresponding anatomical locations should be visible in the angiogram image.

As an exemplary embodiment, the invention stipulates that:

- The catheter contrast injection tip should be visible in both the angiogram images and in the corresponding live images. Shutters may be used, and even displaced between the angiogram and the live phases, provided the injection tip remains visible in both phases.
- At least a second intervention device (typically the guidewire tip or stent/balloon markers) should be present in the live image, and its anatomical location visible in the angiogram image.

Figure 3:
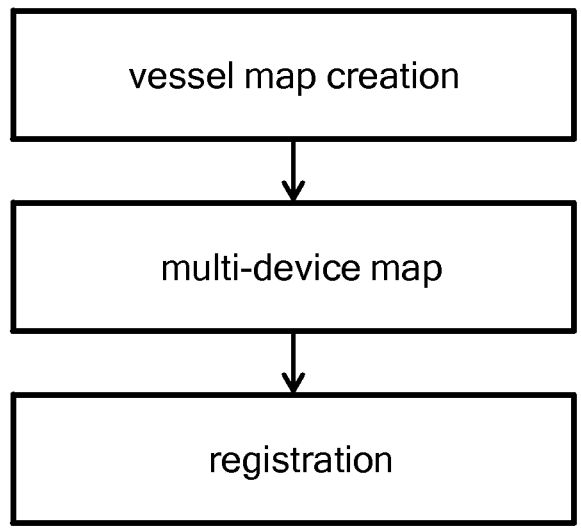
FIG. 3 shows a flow-chart of an exemplary embodiment of a method according to the present invention.

FIG. 3 shows a flow-chart of an exemplary embodiment of a detection/registration method according to the present invention.

Step 1: Vessel map creation

The method relies on the construction of a vessel map, which may simply be a vessel segmentation image or a map that provides, for each pixel, the likelihood of vessel presence. Following a preferred embodiment of the invention, the catheter injection tip should be part of this vessel map.

Step 2: Multi-device map creation

The second step is applied to the live image. It consists in building a device map that accounts for the presence of a least two distinct intervention devices. Those devices are very specific and the map creation method can take advantage of this specificity. For each device nature, a specialised technique might be involved. For instance, one might take into account the device scale, expected breadth and location. In particular, the injection tip is to be looked for near the image borders or shutter borders. When object-specific techniques are used, several device maps might be separately created and then eventually merged into a single multi-device map accounting for all the targeted devices.

The composite device map might be binary, or as in the vessel case, multi-valued, reflecting the likelihood of the presence of each targeted device.

Step 3: Vessel map to device map registration

The registration process may then be applied. It comprises the step of finding the geometrical transformation (among a pre-defined class of possible transformations) that maximizes the similarity between the vessels and the multi-device roadmaps. Several similarity measurements may be considered.

Contrary to [3], it may not be necessary to rely on a distance transform of the vessel map. In [3], that approach was necessary because of the registration uncertainty due to the limited breadth of the device map. With the multi-device map approach more simple approaches may be involved such as the usual correlation methods.

Several other embodiments of this aspect of the present invention may be provided, for example:

- At least two distinct devices must be accounted for in the multi-device map, but the first embodiment described above does not necessarily specify the nature of those devices.
- The first device may be, e.g., the catheter injection tip.
- The second device may be, e.g., the guidewire tip or balloon/stent markers The invention may also be applied to the multiple presence of the same kind of device. For example, several guidewire tips may be used.

Each map (vessel and multi-device) may be either binary (detection case), or multi-valued (enhancement case).

Strong specific considerations, such as: the injection tip should intersect the image border (or shutter borders) may be involved in order to prune the multi-device map from unwanted parasitic objects.

Since very specific intervention devices are looked for, it may be possible to issue a warning to the cardiologist when the detection method fails to identify at least two targeted devices during the multi-device map creation. This may be a way to enforce the proper protocol for cardiac roadmapping.

The way the correspondence between a given live image and its angiogram counterpart is established is not described in the first embodiment. Several specific methods as described in [1], [2] may be applied.

In all the methods described with respect to documents [1], [2], [3], the first step consists of pairing the current live image with a given angiogram image thanks to the matching of their cardiac phases (plus possibly the matching of their respiratory phases).

However, this pairing may rely on the ECG signal or on image-based cardiac phase determination (this is often referred to as the kymogram method).

It should be noted that, when relying on this phase-centric approach, one may be confronted with the following problems:

- The ECG signal is known to be substantially unreliable. In particular, the ECG may be directly connected to the electrical activity, which does not perfectly predict the mechanical muscular activity (producing the motions we want to compensate for).
- The image-based cardiac phase determination methods may also be very error-prone.
- Due to all sort of arrythmic disorders, the cardiac phases may not always be well determined and can be very irregular.
- There can be significant changes in the cardiac rhythm between the angiogram and the live phases. In particular the cardiac rhythm may be substantially impacted by the contrast agent injection.
- Concerning the respiratory phases, the same problems may apply. The respiratory phases can be difficult to identify. They can be irregular.
- As with the cardiac cycles, the respiratory pace during contrast injection often differs from the pace observed in the live phase of the intervention. What is more, not only the pace, but the breathing "depth" also often varies between the angiogram and the live times, which creates unexpected motion discrepancies.

For all those reasons, any method that strongly relies on the cardiac/respiratory phase correlation between the angiogram and the live parts of the intervention may naturally be exposed to all sort of robustness problems.

As already mentioned, it may therefore be desirable to have a method that is not phase-centric.

According to a further aspect of the present invention, a cardiac roadmapping technique is provided that does not rely on the prerequisite of a phase-centric pairing of the angiogram and live images. Instead, both the pairing and accurate registration of the angiogram and live images are combined within a single operation. This operation comprises a global registering of a (causal) device-map sequence, incrementally built at live time, with a vessel-map sequence built during angiogram creation. This global motion-compensated association process relies on map similarities, but may also enforce temporal coherency.

Therefore, knowledge of the cardiac (and respiratory) phases may not be necessary any more. In particular, the invention may produce a cardiac roadmap without the help of any ECG signal or its image-based surrogate (kymogram).

The invention may lead to a more robust cardiac roadmapping, capable of coping with arrythmic disorders, cardiac rhythm instabilities, and respiratory cycle or depth changes.

Figure 4:
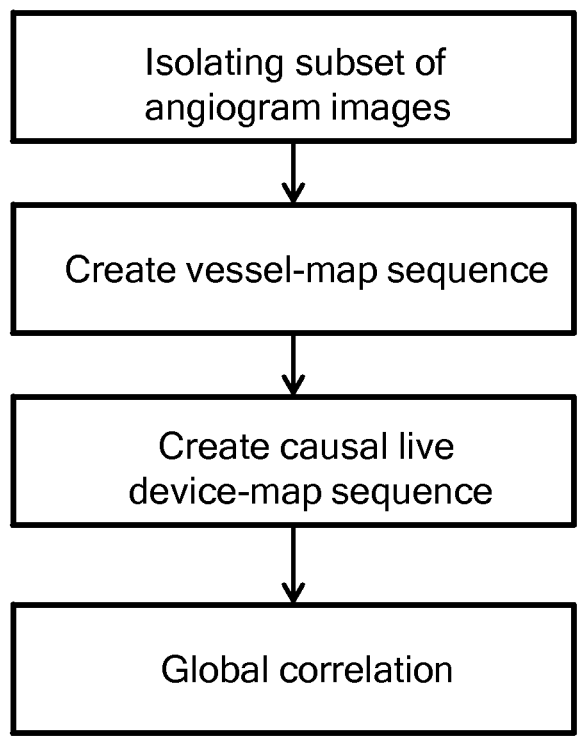
FIG. 4 shows a flow-chart of another exemplary embodiment of a method according to the present invention.

FIG. 4 shows a flow-chart of another exemplary embodiment of a method according to the present invention.

Step 1: Determination of the useful part of the angiogram

The first step consists of isolating from the total angiogram sequence a subset of consecutive images that contains a sufficient amount of contrast agent, thus featuring a good contrast of the vessels set against the background. Simple histogram-based or thresholding techniques applied to the vessel-enhanced angiogram images (the enhancement being performed following for instance [4]) may be used to compute this subset isolation.

Step 2: Creation of a vessel-map sequence from the useful angiogram part

A vessel-map image refers to an image where the pixel values are representative of the likelihood of vessel presence at that pixel. The values can either be binary (designating presence or absence certainty), or they can vary within a certain range, thus measuring a degree of presence likelihood.

Typically, a vessel-map image can be built from a vessel-enhanced image, using for instance the approach described in [4]. But many other techniques are also possible.

Typically, a vessel-map sequence may simply be constituted of vessel-map images, as described above.

However, it may also be the case that the full input sequence (the useful angiogram part) is used to compute each elementary vessel-map image of the sequence. This is typically the case when motion information is used to discriminate between vessel and non-vessel structures.

Also, the vessel-presence likelihood may be replaced or augmented with a vessel-proximity likelihood, for instance using a distance transform.

Step 3: Creation of a causal live device-map sequence up until the current time

As for the vessel-map sequence, a causal device-map sequence is built. The considered devices may for instance be, but not exclusively, the guidewire tip or balloon/stent markers.

The term "causal" simply refers to the fact that the device-map sequence is built up to the current time and no further. Of course, the device-map sequence up to time t can be built from the device-map computed up to t-1, augmented with a device-map at time t. However, this is not necessarily the case.

As in the vessel-map discussion, the notions of:
likelihood of presence of the device,
device enhancement technique,
motion discrimination,
likelihood of device proximity,
may also apply to the case of the device-map sequence.

Step 4: Global correlation of the causal device-map and vessel-map sequences

This final part may be the most important step according to this exemplary embodiment of the present invention.

First a certain class of geometrical transforms is defined. This can for instance be the class of all the translations belonging to a certain range. But this can also encompass other rigid transforms (rotation, sheering, etc. . . . ), or even non-rigid transforms.

Now, within the bound of the transformation class, all the geometrically transformed causal device-maps can be compared via a given similarity criterion to all the vessel-maps of the useful angiogram part (now simply referred to as the angiogram).

The similarity between the device-map Di and vessel-map Vj for the transformation Tk (assuming that the acceptable transforms are indexed by the mono-dimensional index k) is referred to as S[Di, Vj, Tk].

A possible association A between the vessel-map and device-map sequences up to time t can then be represented by the series:

$$A=(j_0, k_0), \ldots (j_u, k_u), \ldots (j_t, k_t)$$

where the subscript u designates the index of the device-map that is associated to the vessel-map of index $j_u$ which is transformed by transform $k_u$ in order to fit to device-map u. Index t designates the current time.

It should be noted that $j_u=f(u)$ and $k_u=g(u)$ are the two elementary association functions that relate a given device-map to a vessel-map and a transformation.

Now, the goal is to find the association A that optimizes a measure function K[A], which symbolically depends on two terms C[A] and H[A]. Typically:

$$K[A]=C[A]+H[A]$$

Term C[A] measures the overall similarity between the device-maps and the transformed vessel-maps. It is a function of the similarity values: $S[Du, Vj_u, Tk_u]$ for u in [0,t]. For instance:

$$C[A] = \sum_{u \in [0,t]} S[Du, Vj_u, Tk_u]$$

Term H[A] enforces the temporal coherency of the association A over the full interval [0, t]. This terms aims at capturing the continuous nature of the image acquisition process and of the involved respiratory and cardiac motions.

For instance:
Between u and u+1, $j_u$ and $j_{u+1}$ must point to vessel-maps that are close together. This closeness may be simply estimated by the distance between the angiogram indices: distM($j_u$, $j_{u+1}$), where dist takes into account the discontinuity existing between the last and the first image of the angiogram (not necessarily purely cyclic). But this closeness may also be estimated by the similarity between the considered vessel maps. Example: distM($j_u$, $j_{u+1}$)=$S[Vj_u, Vj_{u+1}, Id]$ where Id refers to the identity transform.

Between u and u+1, the transforms used to register the two corresponding pairs of device and vessel maps should be close together. This closeness is estimated by a distance distT($Tk_u$, $Tk_{u+1}$). For instance, if Tk directly refers to a translation vector, distT($Tk_u$, $Tk_{u+1}$)=$\|Tk_{u+1}-Tk_u\|$.

As a typical example, the best global association may be computed as:

$$A*[t] = \underset{A}{\mathrm{ArgMax}} \left( \sum_{u \in [0,t]} S[Du, Vj_u, Tk_u] + \alpha S[Vj_u, Vj_{u+1}, Id] - \beta \|Tk_{u+1} - Tk_u\| \right)$$

The terms α and β are simple normalisation constants, and the negative sign in front of β simply accounts for the fact that one looks for high map similarity values, but low inter-transform distance values.

Finally, if the optimum global association up until time t is:

$$A^*[t]=((f^*(0), g^*(0)), \ldots (f^*(u), g^*(u)), \ldots (f^*(t), g^*(t)))$$

then the best matching roadmap for live image t is R*(t):

$$R^*(t)=Tg^*(t) [Vf^*(t)]$$

In this final equation, it may be clearly seen that both the association between a live image (indexed by t) and an angiogram image (indexed, as its vessel-map, by f*(t)) is deduced at the same time as the best registration transform (Tg*(t)). The uniqueness of this process is a key element of this exemplary embodiment of the invention.

Several other embodiments may be provided, for example:

Step a) is optional

Several ways of computing step b) may be provided

Several ways of computing step c) may be provided

In step d), the device-map is not necessarily causal

In step d), the similarities S[Di, Vj, Tk] may have several definition. In particular, the transform can be applied on the map Di so that they match the map Vj (instead of the contrary). In this case, the inverse transform is needed to eventually compute the roadmap. The transform can even be split in two transforms T1k and T2k, one being applied on Di and the other being applied on Tk so that the result of the two transforms shows a good match. In this case, the final roadmap is computed using the composition of T2k and the inverse of T1k.

In step d), the temporal coherency term may be omitted.

In step d), the total measure function K[A] is not necessary the sum of the two terms C[A]+H[A], but the combination of elementary terms that depend on elementary similarities between vessel/device maps, and that might depend on elementary temporal coherency terms.

In step d), K[A] may be limited to time t terms.

In step d), several other example of enforcing temporal coherence in the global association process mya be depicted.

In step d), several ways of optimising function K[A] may be specified.

In step d), the roadmap actually used for the overlay with the live image may not be necessarily identical to the best-transformed vessel-map. It can also be derived from a filtering/extraction operation applied to the corresponding angiogram registered with the same transform (Tg*(t)).

Figure 5:
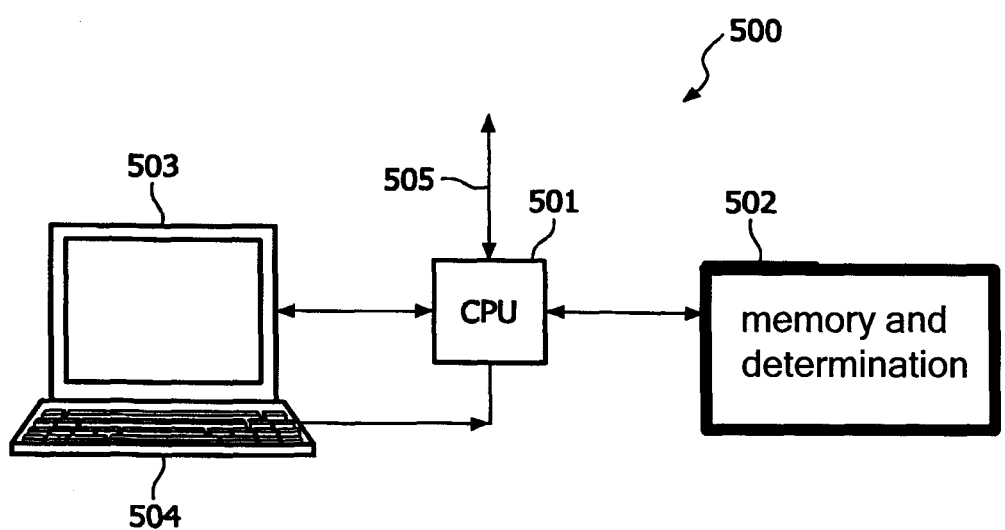
FIG. 5 shows an exemplary embodiment of an image processing device according to the present invention, for executing an exemplary embodiment of a method in accordance with the present invention.

FIG. 5 shows an exemplary embodiment of a data processing device 500 according to the present invention for executing an exemplary embodiment of a method in accordance with the present invention.

The data processing device 500 depicted in FIG. 5 comprises a central processing unit (CPU) or image processor 501 connected to a memory 502 for storing an image depicting an object of interest, such as the heart of a patient or an item of baggage. The central processing unit 502 may comprise a determination unit (not depicted in FIG. 5) according to an aspect of the present invention.

The data processor 501 may be connected to a plurality of input/output network or diagnosis devices, such as a computer tomography scanner. The data processor 501 may furthermore be connected to a display device 503, for example, a computer monitor, for displaying information or an image computed or adapted in the data processor 501. An operator or user may interact with the data processor 501 via a keyboard 504 and/or other input or output devices, which are not depicted in FIG. 5.

Furthermore, via the bus system 505, it may also be possible to connect the image processing and control processor 501 to, for example, a motion monitor, which monitors a motion of the object of interest. In case, for example, a lung of a patient is imaged, the motion sensor may be an exhalation sensor. In case the heart is imaged, the motion sensor may be an electrocardiogram. However, such ECG or exhalation data are, according to an aspect of the invention, not necessary.

Cardiac roadmapping according to the invention is perceived as a possible breakthrough since it may offer to the cardiologist an unprecedented way of achieving PTCA interventions with less contrast agent, less dose, less time, and more security.

According to a further aspect of the present invention, the global correlation determination comprises an optimisation of a measure function K[A], which relates to the similarity.

According to a further aspect of the present invention, the optimisation of the measure function enforces a temporal coherency H[A].

According to a further aspect of the present invention, the device-map sequence is a causal device-map sequence.

According to a further aspect of the present invention, the vessel-map sequence is generated from one of an angiogram data set and an isolated sub-set of the angiogram data set, wherein the vessel-map sequence comprises a plurality of vessel-map images.

According to a further aspect of the present invention, a vessel-map image of the vessel-map sequence is generated on the basis of a vessel-enhanced image.

According to a further aspect of the present invention, each vessel-map image of the vessel-map sequence is computed on the basis of a full isolated sub-set of the angiogram data set.

According to a further aspect of the present invention, an isolation of a sub-set of the angiogram data set is performed on the basis of at least one of a histogram-based and a threshold-based procedure.

According to a further aspect of the present invention, the device-map sequence is generated from a life-image data set.

According to a further aspect of the present invention, the device-map sequence is generated on the basis of at least one of a position of a guidewire or a marker.

According to a further aspect of the present invention, the object of interest is a vessel-tree.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

REFERENCES

[1] "Associating stored images with current images", K. Eck, G. Gijsbers, S. Mollus Patent WO 2004034329 A2, publication date Dec., 02, 2004.

[2] "Device and method for providing an angiographic image", K. Eck, J. Bredno, P. Rongen Patent WO 2005039253 A1, publication date Apr., 28 2005.

[3] "Algorithmic Solutions for Live Device-to-Vessel Match". J. Bredno, B. Martin-Leung & K. Eck. In Proceedings of SPIE-Volume 5370-Medical Imaging 2004: Image Processing, J. Michael Fitzpatrick, Milan Sonka, Editors, May 2004, pp. 1486-1497.

[4] "Multiscale Vessel Enhancement and Filtering", A. Frangi, W. Niessen, K. Vincken, M. Viergever, in Lecture Notes in Computer Science, vol. 1496, pp 130-137, 1998.

The invention claimed is:

1. An examination apparatus for cardiac roadmapping for examination of an object of interest, the examination apparatus comprising:
   an image processor configured for performing a cardiac roadmapping, the image processor comprising a memory for storing data sets of images of the object of interest and first and second devices, including a vessel-map sequence, and a causal live device-map sequence of the first and second devices, the image processor being configured for performing a registration transform between the vessel-map sequence and the causal live device-map sequence;
   a determination processor configured for performing a global correlation determination of the vessel-map sequence and the causal live device-map sequence;
   wherein the global correlation determination is the optimum of the association between the vessel-map sequence and the causal live device-map sequence, based on their overall similarity and temporal coherency, wherein the optimum of the association is deduced at the same time as the registration transform between the vessel-map sequence and the causal live device-map sequence; and
   a display for displaying images from vessel-map sequences or device-map sequences or both.

2. The examination apparatus of claim 1,
   wherein the object of interest is a vessel, and at least one of the images of the vessel-map sequence is binary or multi-valued, reflecting a likelihood of the presence of the vessel.

3. The examination apparatus of claim 1,
   wherein the object of interest is a vessel-tree;
   wherein the first device is a catheter injection tip and the second device is a guidewire or a balloon marker or a stent marker.

4. The examination apparatus of claim 1,
   wherein the examination apparatus is further configured to display an alarm on the display if no detection of the first device or the second device is made.

5. The examination apparatus of claim 1, wherein the determination processor is configured to perform the global correlation determination using rigid and non-rigid registration transforms.

6. The examination apparatus of claim 1, wherein the determination processor is configured to perform the global correlation determination by comparison of device-maps of the device-map sequence to vessel-maps of the vessel-map sequence, resulting in a similarity $S[D_i, V_j, T_k]$ between each device-map of the device-map sequence and each vessel-map of the vessel-map sequence.

7. A system for medical application comprising a rotational X-ray device and the examination apparatus of claim 1, wherein the examination apparatus receives images from the rotational X-ray device.

8. A method for cardiac roadmapping for examination of a vessel-tree, the method comprising:
   performing a cardiac roadmapping and storing in a memory in an image processor data sets of images of the vessel-tree and first and second devices, including a vessel-map sequence, and a causal live device-map sequence of the first and second devices;
   performing a registration transform between the vessel-map sequence and the causal live device-map sequence;
   performing a global correlation determination by using a determination processor for determining-the optimum of the association between the vessel-map sequence and the causal live device-map sequence, based on their overall similarity and temporal coherency, wherein the optimum of the association is deduced at the same time as the registration transform between the vessel-map sequence and the causal live device-map sequence; and
   displaying images from vessel-map sequences or device-map sequences or both.

9. A computer program product including computer data stored on a non-transitory computer readable medium, the computer program product comprising program code instructions to perform the steps of:
   performing a cardiac roadmapping and storing in a memory in an image processor data sets of images of a vessel-tree and first and second devices, including a vessel-map sequence, and a causal live device-map sequence of the first and second devices;
   performing a registration transform between the vessel-map sequence and the causal live device-map sequence;
   performing a global correlation determination by using a determination processor for determining-the optimum of the association between the vessel-map sequence and the causal live device-map sequence, based on their overall similarity and temporal coherency, wherein the optimum of the association is deduced at the same time as the registration transform between the vessel-map sequence and the causal live device-map sequence; and
   displaying images from vessel-map sequences or device-map sequences or both.

* * * * *